US012714658B2

(12) United States Patent
Kim et al.

(10) Patent No.: US 12,714,658 B2
(45) Date of Patent: Aug. 25, 2026

(54) OIL-IN-WATER EMULSIFIED COSMETIC

(71) Applicant: L V M H RECHERCHE, Saint-Jean de Brave (FR)

(72) Inventors: Bora Kim, Chiyoda-Ku (JP); Mai Ozawa, Chiyoda-Ku (JP)

(73) Assignee: L V M H RECHERCHE, Saint-Jean de Braye (FR)

( * ) Notice: Subject to any disclaimer, the term of this patent is extended or adjusted under 35 U.S.C. 154(b) by 591 days.

(21) Appl. No.: 17/787,269

(22) PCT Filed: Dec. 19, 2019

(86) PCT No.: PCT/IB2019/001401

§ 371 (c)(1),
(2) Date: Jun. 17, 2022

(87) PCT Pub. No.: WO2021/123857

PCT Pub. Date: Jun. 24, 2021

(65) Prior Publication Data

US 2023/0021975 A1 Jan. 26, 2023

(51) Int. Cl.
*A61K 8/36* (2006.01)
*A61K 8/06* (2006.01)
(Continued)

(52) U.S. Cl.
CPC .............. *A61K 8/361* (2013.01); *A61K 8/062* (2013.01); *A61K 8/33* (2013.01); *A61K 8/375* (2013.01);
(Continued)

(58) Field of Classification Search
CPC . A61K 8/361; A61K 8/39; A61K 8/37; A61K 8/062; A61K 8/375; A61K 8/8152; A61K 8/922; A61K 8/86; A61K 8/342; A61K 8/8147; A61K 2800/48; A61K 8/06; A61K 8/31; A61K 8/345; A61K 8/8158; A61K 8/891; A61K 8/73; A61K 2800/30; A61K 8/92; A61K 8/35; A61K 8/585; A61K 8/40; A61K 8/042; A61K 8/064; A61K 8/29; A61K 2800/54; A61K 8/895; A61K 2800/548; A61K 8/26; A61K 8/671; A61K 8/731; A61K 2800/20; A61K 8/34; A61K 8/365; A61K 8/368; A61K 8/42; A61K 8/44; A61K 8/442; A61K 8/678; A61K 2800/5426; A61K 8/046; A61K 8/19; A61K 8/602; A61K 2800/10; A61K 2800/52; A61K 8/36; A61K 8/817; A61K 8/8182; A61K 8/33; A61K 8/4993; A61K 2800/42; A61K 2800/524; A61K 2800/5422; A61K 2800/594; A61K 8/22; A61K 8/41; A61K 8/463; A61K 8/498; A61K 8/60; A61K 8/604; A61K 8/676; A61K 8/732; A61K 8/81; A61K 8/894; A61K 2800/34; A61K 2800/49; A61K 2800/5424; A61K 2800/5428; A61K 2800/596; A61K 2800/882; A61K 8/25; A61K 8/466; A61K 8/4973; A61K 8/55; A61K 8/8129; A61K 8/8176; A61K 8/8188; A61K 8/87; A61K 8/89; A61K 8/9794; A61K 2800/26; A61K 2800/262; A61K 2800/28; A61K 2800/412; A61K 2800/413; A61K 2800/432; A61K 2800/51; A61K 2800/522; A61K 2800/5922; A61K 2800/622; A61K 2800/651; A61K 2800/75; A61K 2800/805; A61K 2800/87; A61K 2800/88; A61K 47/12; A61K 8/0208; A61K 8/0229; A61K 8/0241; A61K 8/04;
(Continued)

(56) References Cited

U.S. PATENT DOCUMENTS 6,835,700 B1 12/2004 Nieendick et al.
2013/0156831 A1* 6/2013 Matsuo .................... A61K 8/73 514/772.3

FOREIGN PATENT DOCUMENTS

EP 3636249 A1 4/2020
JP 2019019077 A 2/2019
(Continued)

OTHER PUBLICATIONS

Paula's Choice Behenic Acid [online], [retrieved on Dec. 12, 2024], retrieved online <https://www.paulaschoice.com/ingredient-dictionary/ingredient-behenic-acid.html?q=Behenic%20Acid&fdid=ingredients>. (Year: 2024).*
(Continued)

*Primary Examiner* — Audrea B Coniglio
(74) *Attorney, Agent, or Firm* — Panitch Schwarze Belisario & Nadel LLP; Erin M. Dunston

(57) ABSTRACT

The invention provides an oil-in-water emulsified cosmetic containing (a) an aqueous medium, (b) two or more higher fatty acids of 12 to 24 carbon atoms and alkali metal salts thereof,
(c) at least one compound selected from the group consisting of monoalkyl glyceryl ethers having an alkyl group of 12 to 24 carbon atoms and monoalkenyl glyceryl ethers having an alkenyl group of 12 to 24 carbon atoms,
(d) a thickener comprising (d-1) a polysaccharide derived from a microorganism and (d-2) a (meth)acrylic-based polymer selected from the group consisting of a poly (meth)acrylic acid salt and a polymer including at least one selected from the group consisting of a (meth) acrylic acid ester, a (meth)acryloylalkyltaurine and a salt thereof as a structural unit, and
(e) a nonionic surfactant.

2 Claims, No Drawings

(51) Int. Cl.

| | |
|---|---|
| ***A61K 8/33*** | (2006.01) |
| ***A61K 8/37*** | (2006.01) |
| ***A61K 8/42*** | (2006.01) |
| ***A61K 8/73*** | (2006.01) |
| ***A61K 8/81*** | (2006.01) |
| ***A61Q 1/02*** | (2006.01) |

(52) U.S. Cl.

CPC .................. *A61K 8/42* (2013.01); *A61K 8/73* (2013.01); *A61K 8/8147* (2013.01); *A61Q 1/02* (2013.01); *A61K 2800/436* (2013.01); *A61K 2800/48* (2013.01)

(58) Field of Classification Search

CPC . A61K 8/068; A61K 8/20; A61K 8/24; A61K 8/27; A61K 8/30; A61K 8/416; A61K 8/43; A61K 8/46; A61K 8/496; A61K 8/4966; A61K 8/64; A61K 8/65; A61K 8/68; A61K 8/733; A61K 8/736; A61K 8/737; A61K 8/8105; A61K 8/8111; A61K 8/8117; A61K 8/90; A61K 8/925; A61K 8/9789; A61Q 5/02; A61Q 19/00; A61Q 17/04; A61Q 19/10; A61Q 5/00; A61Q 5/06; A61Q 1/06; A61Q 1/02; A61Q 5/12; A61Q 1/08; A61Q 15/00; A61Q 5/065; A61Q 19/007; A61Q 19/08; A61Q 1/00; A61Q 1/10; A61Q 19/001; A61Q 19/02; A61Q 1/04; A61Q 1/12; A61Q 1/14; A61Q 19/005; A61Q 19/008; A61Q 19/06; A61Q 5/04; A61Q 9/00

See application file for complete search history.

(56) References Cited

FOREIGN PATENT DOCUMENTS

| | | | |
|---|---|---|---|
| KR | 20130102641 | A | 9/2013 |
| WO | WO-2010/046406 | A2 | 4/2010 |
| WO | WO-2013102567 | A2 | 7/2013 |
| WO | WO-2018221606 | A1 | 12/2018 |

OTHER PUBLICATIONS

Paula's Choice Stearic Acid [online], [retrieved on Dec. 12, 2024], retrieved online <https://www.paulaschoice.com/ingredient-dictionary/ingredient-stearic-acid.html?q=stearic%20acid&fdid=ingredients>. (Year: 2023).*

Paula's Choice Glyceryl Stearate [online], [retrieved on Dec. 13, 2024], retrieved online <https://www.paulaschoice.com/ingredient-dictionary/ingredient-glyceryl-stearate.html?q=Glyceryl%20Stearate&fdid=ingredients>. (Year: 2023).*

Paula's Choice PEG-30 Stearate [online], [retrieved on Dec. 13, 2024], retrieved online <https://www.paulaschoice.com/ingredient-dictionary/ingredient-peg-30-stearate.html?srsltid=AfmBOorJu_cCOFH80bj6h75iOFGBpHxhZ9fmbkzXslo38dv0iuwzCQ2E>. (Year: 2023).*

B&C Laboratories "Prize Charge Cream", GNPD, Mintel, Dec. 1, 2009.

B&C Laboratories "Aminoeffectivesleep Cream", VECUA Skinperfectsphere, p. 1-3, Sep. 1, 2009.

Perricone MD Cosmeceauticlas, "Firming & Illuminating Under-Eye Cream" GNPD, Mintel, Jan. 4, 2019.

International Search Report and Written Opinion for Corresponding International Application No. PCT/IB2019/001401, mailing date Sep. 15, 2020.

Notice of Preliminary Rejection issued in counterpart Korean Application No. 10-2022-7023260 on Feb. 13, 2025.

* cited by examiner

OIL-IN-WATER EMULSIFIED COSMETIC

CROSS REFERENCE TO RELATED APPLICATIONS

This application is a U.S. National Stage of International Patent Application No. PCT/IB2019/001401 filed Dec. 19, 2019, the disclosure of which is incorporated herein by reference in their entirety.

TECHNICAL FIELD

The present invention relates to an oil-in-water emulsified cosmetic.

BACKGROUND ART

Skin care products having a pearlescent appearance have been known so far, the pearlescent appearance being produced by a pearlescent pigment such as mica/tin oxide. However, since such pearlescent pigments cause pore clogging and skin dryness, skin care products containing pearlescent pigments are generally not popular among consumers.

Cosmetics that produce a pearlescent appearance without pearlescent pigments have been proposed, examples of which include a cosmetic composition containing a wax such as an alkylene glycol ester, an emulsifier and a polyol ester as disclosed in U.S. Pat. No. 6,835,700, and a cosmetic composition containing a higher fatty acid and an alkali metal higher fatty acid soap as disclosed in WO2010/046406.

Technical Problem

Because the cosmetic compositions described in the said prior art contain large amounts of wax or higher fatty acids, they have been problematic as they are highly viscous and produce stickiness or a heavy feeling when applied.

So it is an object of this invention to provide a stable oil-in-water emulsified cosmetic that has a pearlescent appearance without containing a pearlescent pigment, and that can impart a light texture when applied. As used herein, the term "pearlescent appearance" means a pearly appearance which is visually evaluated by putting 1 mg of an oil-in-water emulsified cosmetic on a black plate. The composition of the invention then provides, when applied onto the skin, a luminous or radiant complexion, for a skin appearing younger.

SUMMARY OF INVENTION

The invention provides an oil-in-water cosmetic comprising (a) an aqueous medium, (b) two or more higher fatty acids of 12 to 24 carbon atoms, or their alkali metal salts, (c) at least one compound selected from the group consisting of monoalkyl glyceryl ethers having alkyl groups of 12 to 24 carbon atoms and monoalkenyl glyceryl ethers having alkenyl groups of 12 to 24 carbon atoms, (d) a thickener comprising (d-1) a polysaccharide derived from a microorganism and (d-2) a (meth)acrylic-based polymer selected from the group consisting of a poly(meth)acrylic acid salt and a polymer including at least one selected from the group consisting of a (meth)acrylic acid ester, a (meth)acryloylalkyltaurine and a salt thereof as a structural unit, and (e) a nonionic surfactant. The "(a) aqueous medium" may also be referred to hereunder simply as "component (a)", and the other components may be referred to in a similar manner. As used herein, the term "(meth)acrylic" refers to acrylic or methacrylic, with the same applying to analogous backbones.

The oil-in-water emulsified cosmetic of the invention may also further contain (f) a ceramide. By containing component (f) it can provide additional moisture during application.

In the oil-in-water emulsified cosmetic of the invention, the nonionic surfactant (e) is suitably at least one selected from the group consisting of glycerin fatty acid esters, fatty acid polyethylene glycols, polyglycerin fatty acid esters, and mixtures thereof. The stability of the oil-in-water emulsified cosmetic will thus be even more excellent.

The viscosity of the oil-in-water emulsified cosmetic of the invention at 25° C. is suitably no higher than 2000 mPa·s. If the viscosity is within this range it will be possible to impart a lighter texture during application.

The invention also concerns a cosmetic process for caring for and/or making-up keratinic materials comprising the application onto keratinic materials, in particular onto skin, of the oil-in-water emulsified cosmetic as defined in the invention. In particular, the cosmetic process of the invention provides a luminous or radiant complexion onto the skin.

Advantageous Effects of Invention

According to the invention, it is possible to provide a stable oil-in-water emulsified cosmetic that has a pearlescent appearance without containing a pearlescent pigment, and that can impart a light texture when applied.

DETAILED DESCRIPTION OF THE INVENTION

Preferred embodiments of the invention will now be described, with the understanding that these embodiments are in no way limitative on the invention.

Aqueous Phase

The oil-in-water emulsified cosmetic of this embodiment contains an aqueous medium (a). The aqueous medium may consist of water alone, or it may also include a solvent that is soluble in water.

The water used may be distilled water, purified water, hot spring water, deep water, or plant-derived steam distilled water such as lavender water, rose water or orange flower water.

Examples of solvents that are soluble in water include mono-alcohols such as methanol, ethanol, propyl alcohol, isopropyl alcohol and phenoxyethanol; and polyhydric alcohols such as ethylene glycol, 1,3-propanediol, propylene glycol, butylene glycol, pentylene glycol, hexylene glycol, dipropylene glycol, polyethylene glycol, glycerin, diglycerin, polyglycerin, sorbitol, xylitol and mannitol. The solvent that is soluble in water may be a single one used alone, or two or more may be used in combination.

The content of the aqueous medium (a) is preferably 80 to 95 mass % and more preferably 90 to 95 mass % based on the total mass. As used herein, "based on the total mass" means based on the total mass of the oil-in-water emulsified cosmetic. The "mass %" may also be referred to hereunder as "% by weight".

Higher Fatty Acids

The oil-in-water emulsified cosmetic of this embodiment contains (b) two or more higher fatty acids of 12 to 24 carbon atoms, or their alkali metal salts.

Examples of higher fatty acids of 12 to 24 carbon atoms include lauric acid, myristic acid, palmitic acid, stearic acid, isostearic acid, arachidic acid, behenic acid, palmitoleic acid, oleic acid, linolic acid and linolenic acid.

Examples of alkali metal salts of higher fatty acids of 12 to 24 carbon atoms include their sodium salts and potassium salts.

Examples of combinations of two or more higher fatty acids of 12 to 24 carbon atoms or their alkali metal salts include two or more selected from the group consisting of lauric acid, myristic acid, palmitic acid, stearic acid, isostearic acid, behenic acid, oleic acid, linolic acid, linolenic acid and their alkali metal salts. Preferred among these are combinations of two selected from the group consisting of palmitic acid, stearic acid, behenic acid and their alkali metal salts, as they allow brighter pearlescence to be exhibited, with combinations of stearic acid or its alkali metal salts and behenic acid or its alkali metal salts being more preferred.

The content of component (b) ranges preferably from 0.1 to 5 mass % and more preferably from 0.5 to 3 mass % based on the total mass. If the content of component (b) is within this range, the pearlescent appearance of the oil-in-water emulsified cosmetic will be more satisfactory and an even lighter texture can be imparted when it is applied.

Ethers

The oil-in-water emulsified cosmetic of this embodiment contains (c) at least one compound selected from the group consisting of monoalkyl glyceryl ethers having alkyl groups of 12 to 24 carbon atoms and monoalkenyl glyceryl ethers having alkenyl groups of 12 to 24 carbon atoms.

Monoalkyl glyceryl ethers having alkyl groups of 12 to 24 carbon atoms and monoalkenyl glyceryl ethers having alkenyl groups of 12 to 24 carbon atoms are a group of compounds in which a higher alcohol of 12 to 24 carbon atoms and one of the hydroxyl groups of a glycerin molecule form an ether bond.

Examples of monoalkyl glyceryl ethers having alkyl groups of 12 to 24 carbon atoms include monolauryl glyceryl ether, monomyristyl glyceryl ether, monocetyl glyceryl ether (chimyl alcohol), monostearyl glyceryl ether (batyl alcohol), monoisostearyl glyceryl ether, monoarachidyl glyceryl ether and monobehenyl glyceryl ether. Examples of monoalkenyl glyceryl ethers having alkenyl groups of 12 to 24 carbon atoms include monopalmitoleyl glyceryl ether, monooleyl glyceryl ether (selachyl alcohol), monolinoleyl glyceryl ether and monolinolenyl glyceryl ether. Component (c) may be a single compound used alone, or two or more may be used in combination. Monostearyl glyceryl ether (batyl alcohol) is preferred among these component (c) compounds as it allows brighter pearlescence to be exhibited.

The content of component (c) ranges preferably from 0.05 to 5 mass % and more preferably from 0.1 to 3 mass % based on the total mass. If the content of component (c) is within this range, the pearlescent appearance of the oil-in-water emulsified cosmetic will be more satisfactory and an even lighter texture can be imparted when it is applied.

It is preferable to use a composition obtained by mixing and heating at least (i) two or more higher fatty acids of 12 to 24 carbon atoms, (ii) at least one compound selected from the group consisting of monoalkyl glyceryl ethers having alkyl groups of 12 to 24 carbon atoms and monoalkenyl glyceryl ethers having alkenyl groups of 12 to 24 carbon atoms and (iii) an alkali metal hydroxide, as component (b) and component (c), since it allows brighter pearlescence to be exhibited. For example, Mizoan® Cerawax-Bril (product of Biobeautech), which contains stearic acid or its potassium salt, behenic acid or its potassium salt, monostearyl glyceryl ether (batyl alcohol) and ceramide 3, may be used as component (b) and component (c).

Thickener

The oil-in-water emulsified cosmetic of this embodiment contains (d) a thickener comprising (d-1) a polysaccharide derived from a microorganism and (d-2) a (meth)acrylic-based polymer.

As used herein, "polysaccharide derived from a microorganism" means a polysaccharide obtained by purifying and processing a substance produced by a microorganism. Examples of polysaccharides derived from microorganisms include xanthan gum, gellan gum, sclerotium gum, *Alcaligenes*-derived polysaccharides and *Tremella fuciformis*-derived polysaccharides. Component (d-1) may be a single one used alone, or two or more may be used in combination. Xanthan gum is preferred for component (d-1) for excellent stability of the oil-in-water emulsified cosmetic.

As used herein, "(meth)acrylic-based polymer" means a polymer that includes (meth)acrylic acid and/or a derivative thereof, such as (meth)acrylic acid, (meth)acrylic acid ester or (meth)acrylamide, as a structural unit. In a particular embodiment, the (meth)acrylic-based polymer is selected from the group consisting of a poly(meth)acrylic acid salt and a polymer including at least one selected from the group consisting of a (meth)acrylic acid ester, a (meth)acryloylalkyltaurine and a salt thereof as a structural unit. The (meth) acrylic-based polymer is preferably hydrophilic. In another embodiment, the (meth)acrylic-based polymer preferably includes at least one selected from the group consisting of a (meth)acrylic acid, a (meth)acrylic acid ester and a (meth) acryloylalkyltaurine and a salt thereof as a structural unit. Specific examples of polymers that include (meth)acrylic acid or a salt thereof as a structural unit include poly(meth) acrylic acid salt (for example, sodium polyacrylate). Specific examples of polymers that include a (meth)acrylic acid ester as a structural unit include (acrylates/C10-30 alkyl acrylate) crosspolymer, (acrylates/ethylhexyl acrylate) copolymer, (acrylates/steareth-20 methacrylate) copolymer and (acrylates/beheneth-25 methacrylate) copolymer. Specific examples of polymers that include (meth)acryloylalkyltaurine or a salt thereof as structural units include (acryloyldimethyltaurine ammonium/beheneth-25 methacrylate) crosspolymer, (hydroxyethyl acrylate/acryloyldimethyltaurine sodiumu) copolymer, (acryloyldimethyltaurine ammonium/VP) copolymer, (acryloyldimethyltaurine ammonium/carboxyethylammonium acrylate) crosspolymer, (acrylamide/acryloyldimethyltaurine sodium) copolymer, (dimethylacrylamide/acryloyldimethyltaurine sodium), crosspolymer (sodium acrylate/acryloyldimethyltaurine/dimethylacrylamide) crosspolymer, (acryloyldimethyltaurine sodium/VP) crosspolymer, polyacryloyldimethyltaurine ammonium, (sodium acrylate/acryloyldimethyltaurine sodium) copolymer and polyacryloyldimethyltaurine sodium. Component (d-2) may be a single one used alone, or two or more may be used in combination. Among these compounds for (d-2), a poly(meth)acrylic acid salt, a polymer including at least one selected from the group consisting of a (meth)acrylic acid ester, a (meth)acryloylalkyltaurine and a salt thereof as a structural unit are preferred, sodium polyacrylate, (acrylates/C10-30 alkyl acrylate) crosspolymer and (acryloyldimethyltaurine ammonium/VP) copolymer are more preferred, and (acryloyldimethyltaurine ammonium/VP) copolymer is further preferred, from the viewpoint of stability in the oil-in-water emulsified cosmetic. As used herein, "VP" refers to vinylpyrrolidone.

Combinations of component (d-1) and component (d-2) for component (d) may be any combination of the different components listed as examples for component (d-1) with the different components listed as examples for component (d-2), among which combinations of xanthan gum and one selected from the group consisting of sodium polyacrylate, (acrylates/C10-30 alkyl acrylate) crosspolymer and (acryloyldimethyltaurine ammonium/VP) copolymer are preferred, and a combination of xanthan gum and (acryloyldimethyltaurine ammonium/VP) copolymer is more preferred, since the stability of the oil-in-water emulsified cosmetic will be particularly excellent.

Component (d) may also contain a polysaccharide other than component (d-1) (for example, hyaluronic acid or its salt, chondroitin sulfate or its salt, guar gum, locust bean gum, pectin, carrageenan, agar, alginic acid or its salt, starch, dextrin or the like), in addition to component (d-1) and component (d-2).

The content of component (d) ranges preferably from 0.1 to 6 mass % and more preferably from 0.2 to 4 mass % based on the total mass. If the content of component (d) is within this range the stability of the oil-in-water emulsified cosmetic will be even more excellent.

The content of component (d-1) in component (d) ranges preferably from 0.05 to 3 mass % and more preferably from 0.1 to 2 mass % based on the total mass. If the content of component (d-1) is within this range the stability of the oil-in-water emulsified cosmetic will be even yet more excellent.

The content of component (d-2) in component (d) ranges preferably from 0.05 to 3 mass % and more preferably from 0.1 to 2 mass % based on the total mass. If the content of component (d-2) is within this range the stability of the oil-in-water emulsified cosmetic will be even yet more excellent.

Nonionic Surfactant

The oil-in-water emulsified cosmetic of this embodiment contains a nonionic surfactant (e).

Examples of nonionic surfactants include glycerin fatty acid esters (for example, glyceryl myristate, glyceryl stearate and glyceryl oleate), sorbitan fatty acid esters (for example, sorbitan monostearate, sorbitan monooleate, sorbitan tristearate and sorbitan trioleate), sucrose fatty acid esters, polyoxyethylene alkyl ethers (for example, polyoxyethylene lauryl ether, polyoxyethylene cetyl ether, polyoxyethylene stearyl ether and polyoxyethylene oleyl ether), polyoxyethylene alkylphenyl ethers, alkyl glucosides (for example, decyl glucoside, lauryl glucoside and cocoglycoside), polyethylene glycol fatty acids (for example, polyethylene glycol monolaurate and polyethylene glycol monostearate) and polyoxyethylene sorbitan fatty acids (for example, polyoxyethylene sorbitan monostearate, polyoxyethylene sorbitan monooleate, polyoxyethylene sorbitan tristearate and polyoxyethylene sorbitan trioleate), and polyglycerin fatty acid esters (for example, polyglyceryl-10 myristate, polyglyceryl-10 stearate and polyglyceryl-10 oleate). The nonionic surfactant used may be a single type alone, or two or more may be used in combination. Component (e) is preferably at least one selected from the group consisting of glycerin fatty acid esters, polyethylene glycol fatty acids and polyglycerin fatty acid esters, and more preferably a combination of glyceryl stearate and polyethyleneglycol stearate, because the stability of the oil-in-water emulsified cosmetic will be excellent.

The content of component (e) ranges preferably from 0.5 to 5 mass % and more preferably from 1 to 4 mass % based on the total mass. If the content of component (e) is within this range the stability of the oil-in-water emulsified cosmetic will be even more excellent.

Ceramide

The oil-in-water emulsified cosmetic of this embodiment may further contain (f) a ceramide. If the oil-in-water emulsified cosmetic contains component (f) it will be able to impart even more moisture when coated onto skin.

Ceramides are a group of compounds having sphingosine and a fatty acid bonded by an amide bond. Specific examples of ceramides include ceramide 1 (ceramide EOP), ceramide 2 (ceramide NG), ceramide 3 (ceramide NP), ceramide 4 (ceramide EOH), ceramide 5 (ceramide AG), ceramide 611 (ceramide AP) and ceramide 9 (ceramide EOS). A single ceramide may be used alone, or two or more may be used in combination. Component (f) is preferably ceramide 3 (ceramide NP), since this will allow even more moisture to be imparted upon application.

The content of component (f) ranges preferably from 0.05 to 3 mass % and more preferably from 0.1 to 2 mass % based on the total mass. If the content of component (f) is within this range it will be possible to impart yet even more moisture when coated onto skin.

Mizoan® Cerawax-Bril (product of Biobeautech), which contains stearic acid or its potassium salt, behenic acid or its potassium salt, monostearyl glyceryl ether (batyl alcohol) and ceramide 3 (ceramid NP), may also be used as component (f).

The oil-in-water emulsified cosmetic of this embodiment may further contain an oil agent. Oil agents include hydrocarbon oils (for example, liquid paraffin, light liquid isoparaffin, dodecane, isododecane, tetradecane, isotetradecane, hexadecane, isohexadecane, squalane, vegetable squalane, vaseline, polyisobutylene and polybutene), fats and oils (for example, Japan wax, olive oil, castor oil, mink oil, macadamia nut oil, camellia oil, rose hip oil and avocado oil), waxes (for example, beeswax, lanolin, carnauba wax, candelilla wax and spermaceti wax), ester oils (for example, jojoba oil, cetyl isooctanate, glyceryl tri(caprylate/caprate), isopropyl myristate, isopropyl palmitate, octyldodecyl myristate, glyceryl trioctanoate (triethylhexanoin), polyglyceryl diisostearate, diglyceryl triisostearate, glyceryl tribehenate, diisostearyl malate, neopentylglycol dioctanoate, cholesterol fatty acid esters and phytosterol fatty acid esters), silicone oils (for example, polydimethylsiloxane (dimethicone), polymethylphenylsiloxane (diphenyldimethicone), phenyltrimethicone, diphenylsiloxyphenyltrimethicone, amino-modified silicone, epoxy-modified silicone, carboxy-modified silicone, polyether-modified silicone, alkyl-modified silicone and fluorine-modified silicone), and fluorine-based oils (for example, perfluoropolyether, perfluorodecalin and perfluorooctane). A single oil agent may be used alone, or two or more may be used in combination. For the purpose of the present specification, an oil agent does not include component (b) or component (c).

The oil-in-water emulsified cosmetic of this embodiment may also contain, in addition to these components, other additives such as pH regulators, chelating agents, antioxidants, antifading agents, antiseptic agents, drug components, stabilizers, powders, pigments and perfumes, added as appropriate in order to impart various effects. The oil-in-water emulsified cosmetic of this embodiment preferably does not contain a pearlescent pigment such as mica/tin oxide to avoid pore clogging and skin dryness.

The 25° C. viscosity of the oil-in-water emulsified cosmetic of this embodiment is preferably no higher than 2000 mPa·s, more preferably no higher than 1500 mPa·s and even more preferably no higher than 1000 mPa·s. If the 25° C.

viscosity is in this range it will be possible to impart a lighter texture during application. The 25° C. viscosity of the oil-in-water emulsified cosmetic of this embodiment is also preferably 100 mPa·s or higher, 500 mPa·s or higher or 600 mPa·s or higher, for example. In a particular embodiment, the viscosity of the composition ranges from 100 mPa·s to 2000 mPa·s, in particular from 500 mPa·s to 1500 mPa·s and preferably from 600 mPa·s to 1000 mPa·s. The viscosity may be measured using a rotating viscometer (for example, Rheolab QC by Anton Paar).

The oil-in-water emulsified cosmetic of this embodiment can be prepared by the following steps, as an example.

1) Component (a) and other aqueous components as necessary are combined, heated and stirred, and then component (d) is added and the mixture is heated and stirred to obtain an aqueous mixture.
2) Component (b), component (c), component (e) and if necessary component (f), an oil agent and other oil components are mixed, heated and stirred to obtain an oil-based mixture.
3) The oil-based mixture obtained in 2) is added to the aqueous mixture obtained in 1), and the resulting mixture is heated and stirred, and then cooled to room temperature.

The oil-in-water emulsified cosmetic of this embodiment can be suitably used as a skin cosmetic, and is preferably used by application onto the skin (excluding the scalp), and more preferably onto the face, body and limbs. The oil-in-water emulsified cosmetic of this embodiment can be utilized as a latex or essence, for example.

The invention also concerns a cosmetic process for caring for and/or making-up keratinic materials comprising the application onto keratinic materials, in particular onto skin, of the oil-in-water emulsified cosmetic as defined above. In particular, the cosmetic process provides a luminous or radiant complexion onto the skin.

EXAMPLES

The present invention will now be explained in specific detail through the following examples, with the understanding that the invention is not limited by the examples.

(1) Preparation of a composition containing stearic acid or its potassium salt, behenic acid or its potassium salt and batyl alcohol (Mizoan® Cerawax-Bril; Table 1). The stearic acid, behenic acid and batyl alcohol were mixed and heated at 95 to 110° C. to dissolution. Phytostearyl isostearate and ceramide 3 were added to the solution, and stirring was carried out for about 3 hours at 150 to 210° C. Potassium hydroxide was then added, stirring was continued for about 1 hour at 80 to 95° C., citric acid was further added, and stirring was continued at 70 to 85° C. The obtained mixture was cooled to room temperature to obtain the titled composition.

TABLE 1

| Ingredient | Content (%) |
|---|---|
| Stearic acid | 44 |
| Behenic acid | 20 |
| Batyl alcohol | 12 |
| Phytostearyl isostearate | 8 |
| Ceramide 3 | 8 |
| Potassium hydroxide | 5 |
| Citric acid | 3 |

(2) Preparation of Oil-In-Water Emulsified Cosmetics

Oil-in-water emulsified cosmetics were prepared by the following method, based on the compositions shown in Table 2.

Each of the components in component (a) were mixed at 70° C., and then each of the components in component (d) were added and the mixture was stirred at 70° C. to obtain an aqueous mixture. In addition, Mizoan® Cerawax-Bril (a composition containing component (b), component (c) and component (f)), component (e) and each of the components in the oil agent were mixed, and the mixture was stirred at 80 to 85° C. to obtain an oil-based mixture. After adding the oil-based mixture to the aqueous mixture and stirring at 80 to 85° C., it was cooled to room temperature to obtain different oil-in-water emulsified cosmetics. The ratios (% by mass) of the respective components are as shown in Table 2.

(3) Evaluation of Appearance

The appearance of each cosmetic was visually observed by putting 1 mg of the cosmetic on a black plate and evaluated based on the following scale by an evaluation panel of 13 cosmetic experts.

A: Excellent pearlescent appearance
B: Moderate pearlescent appearance
C: Non-pearlescent appearance (4) Organoleptic Evaluation The lightness of texture during application of each of the cosmetics were evaluated based on the following scale, in a single use test on skin by an evaluation panel of 13 cosmetic experts. As used herein, "the lightness of texture" means a texture of a composition capable of providing watery fresh sensation and good spreadability while applying sample on skin (i.e., the lightness of feel on the skin).

A: Very light texture
B: Light texture
C: Non-light texture (5) Stability Evaluation Each cosmetic was housed in a transparent container and the covering was sealed, after which it was stored at 50° C. for 1 month, and an evaluation of "Y" was assigned when no separation between the oil phase and aqueous phase was observed, while an evaluation of "N" was assigned when separation between the oil phase and aqueous phase was observed.

(6) Viscosity Measurement

The 25° C. viscosity of the each cosmetic was measured using a rotating viscometer (for example, Rheolab QC by Anton Paar, spindle: ST22-4 V, rotational speed: 100 rpm (3 minutes)).

| | Component | Example 1 | Example 2 | Example 3 | Example 4 | Example 5 | Example 6 | Comparative Example 1 | Comparative Example 2 | Comparative Example 3 |
|---|---|---|---|---|---|---|---|---|---|---|
| (a) | Water | Balance | Balance | Balance | Balance | Balance | Balance | Balance | Balance | Balance |
| | Methylpropanediol | 20.00 | 20.00 | 20.00 | 20.00 | — | — | 20.00 | — | — |
| | Glycerin | — | — | — | — | 10.00 | 10.00 | — | 10.00 | 10.00 |
| | Propanediol | — | — | — | — | 8.00 | 5.00 | — | 8.00 | 8.00 |

-continued

| | Component | Example 1 | Example 2 | Example 3 | Example 4 | Example 5 | Example 6 | Comparative Example 1 | Comparative Example 2 | Comparative Example 3 |
|---|---|---|---|---|---|---|---|---|---|---|
| (b) | Stearic Add | 0.66 | 0.66 | 0.66 | 0.66 | 0.88 | 0.88 | 0.44 | 0.88 | 0.88 |
| | Behenic Add | 0.30 | 0.30 | 0.30 | 0.30 | 0.40 | 0.40 | 0.20 | 0.40 | 0.40 |
| (c) | Batyl Alcohol | 0.18 | 0.18 | 0.18 | 0.18 | 0.24 | 0.24 | 0.12 | 0.24 | 0.24 |
| (d) (d-1) | Xanthan Gum | 0.20 | 0.20 | 0.20 | 0.20 | 0.20 | 0.20 | — | 0.20 | — |
| (d) (d-2) | Sodium Polyacrylate | 0.20 | — | — | — | — | — | — | — | — |
| | Acrylates/ C10-30 Alkyl Acrylate Crosspolymer1) | — | 0.20 | 0.20 | — | — | — | — | — | — |
| | Ammonium Acryloyl-dimethyltaurate/ VP Copolymer | — | — | — | 0.20 | 0.20 | 0.20 | — | — | 0.20 |
| (d) other than (d-1) and (d-2) | Sodium Hyaluronate | 0.10 | 0.10 | 0.10 | 0.10 | 0.10 | — | — | 0.10 | 0.10 |
| (e) | Polyglyceryl-10 Myristate | 1.50 | 1.50 | 1.50 | 1.50 | — | — | 1.50 | — | — |
| | Glyceryl Stearate and PEG-100 Stearate | — | — | — | — | 2.00 | 2.00 | — | 2.00 | 2.00 |
| (f) | Ceramide NP | 0.12 | 0.12 | 0.12 | 0.12 | 0.16 | 0.16 | 0.08 | 0.16 | 0.16 |
| oil agent | Squalane | 4.00 | 4.00 | 4.00 | 4.00 | 4.20 | 4.20 | 4.00 | 4.20 | 4.20 |
| others | Phytosteryl Isostearate | 0.12 | 0.12 | 0.12 | 0.12 | 0.16 | 0.16 | 0.08 | 0.16 | 0.16 |
| | Potassium Hydroxide | 0.08 | 0.08 | 0.08 | 0.08 | 0.10 | 0.10 | 0.05 | 0.10 | 0.10 |
| | Citric Add | 0.05 | 0.05 | 0.05 | 0.05 | 0.06 | 0.06 | 0.03 | 0.06 | 0.05 |
| Evaluation results | Appearance | A | A | A | A | A | A | A | A | A |
| | Texture | A | B | B | A | A | A | A | A | A |
| | Stability | Y | Y | Y | Y | Y | Y | N | N | N |
| | Viscosity (mPas) | 676 | 1307 | 1087 | 727 | 710 | 64 S | 516 | 385 | 243 |

The invention claimed is:

1. An oil-in-water emulsified cosmetic comprising:

(a) an aqueous medium, (b) two or more higher fatty acids of 12 to 24 carbon atoms or alkali metal salts thereof, selected from the group consisting of palmitic acid, stearic acid, behenic acid and their alkali metal salts thereof, (c) at least one monostearyl glyceryl ether, (d) a thickener comprising (d-1) xanthan gum and (d-2) a (meth)acrylic-based polymer selected from the group consisting of sodium polyacrylate, acrylates/C10-30 alkyl acrylate crosspolymer and acryloyldimethyltaurine ammonium/VP copolymer (e) a nonionic surfactant, that is a combination of glyceryl stearate and polyethylene glycol stearate, and (f) a ceramide, wherein the viscosity at 25° C. of said oil-in-water emulsified cosmetic is no higher than 2000 mPa·s, and wherein the content of component (b) ranges from 0.5 to 3 mass %, the content of component (c) ranges from 0.1 to 3 mass %, and the content of component (e) ranges from 1 to 4 mass %, based on the total mass, the content of component (f) ranges from 0.05 to 3 mass %, and wherein the content of the thickener ranges from 0.1 to 6 mass % based on the total mass, and wherein the content of the xanthan gum ranges from 0.1 to 2 mass % based on the total mass.

2. A cosmetic process for caring for and/or making-up keratinic materials comprising the application onto keratinic materials of the oil-in-water emulsified cosmetic as defined in claim 1.

* * * * *